United States Patent
Ye et al.

(10) Patent No.: US 10,882,900 B2
(45) Date of Patent: Jan. 5, 2021

(54) MONOCLONAL ANTIBODY OF HUMAN-DERIVED PROCALCITONIN, AND PREPARATION METHOD AND APPLICATION THEREOF

(71) Applicant: Nanjing Norman Biological Technology Co., Ltd., Nanjing (CN)

(72) Inventors: Sen Ye, Nanjing (CN); Shizhao He, Nanjing (CN)

(73) Assignee: Nanjing Norman Biological Technology Co., Ltd., Nanjing (CN)

( * ) Notice: Subject to any disclaimer, the term of this patent is extended or adjusted under 35 U.S.C. 154(b) by 388 days.

(21) Appl. No.: 15/728,480

(22) Filed: Oct. 9, 2017

(65) Prior Publication Data

US 2019/0031744 A1  Jan. 31, 2019

Related U.S. Application Data

(63) Continuation of application No. PCT/CN2016/081545, filed on May 10, 2016.

(30) Foreign Application Priority Data

Jul. 9, 2015 (CN) .......................... 2015 1 0400557
Jul. 16, 2015 (CN) .......................... 2015 1 0419304

(51) Int. Cl.
C07K 16/18 (2006.01)
C07K 16/26 (2006.01)
G01N 33/74 (2006.01)

(52) U.S. Cl.
CPC .............. *C07K 16/18* (2013.01); *C07K 16/26* (2013.01); *G01N 33/74* (2013.01); *C07K 2317/24* (2013.01); *C07K 2317/34* (2013.01); *G01N 2333/585* (2013.01)

(58) Field of Classification Search
None
See application file for complete search history.

(56) References Cited

U.S. PATENT DOCUMENTS

2013/0046085 A1    2/2013   Tavares v zquez et al.

FOREIGN PATENT DOCUMENTS

| CN | 102643332 A | 8/2012 |
|----|----|----|
| CN | 102702324 A | 10/2012 |
| CN | 104745534 A | 7/2015 |
| EP | 1111050 A | 6/2008 |
| WO | WO2008104321 A | 9/2008 |
| WO | WO2010125076 A | 11/2010 |

OTHER PUBLICATIONS

Meyer et al., "New Insights in Type I and II CD20 Antibody Mechanisms-Of-Action With a Panel of Novel CD20 Antibodies", British Journal of Haematology, 2018, 180, 808-820 (Year: 2018).*
Brown et al., "Tolerance of single, but not multiple, amino acid replacements in antibody VH CDR 2: a means of minimizing B cell wastage from somatic hypermutation?", J Immunol. May 1996;156(9):3285-91 (Year: 1996).*
Vajdos et al., "Comprehensive functional maps of the antigen-binding site of an anti-ErbB2 antibody obtained with shotgun scanning mutagenesis" J Mol Biol. Jul. 5, 2002;320(2):415-28 (Year: 2002).*
Zheng, Yilin, Preparation and identification of specific monoclonal antibody against human calcitonin and its preliminary application, Third Military Medical University academic journal, 35th volumes, No. 6, p. 523-526, Mar. 30, 2013.
Kramer Petra M et al:: "Development and characterization of new rat monoclonal antibodies for procalcitonin", Analytical and Bioanalytical Chemistry, Springer, Berlin, DE, vol. 392, No. 4, Oct. 1, 2008 (Oct. 1, 2008), pp. 727-736, XP002584671.
WO2017005048—International Preliminary Examination Report, (7 pages).
CN105801697A—First office action, (11 pages)

* cited by examiner

*Primary Examiner* — Ellen J Marcsisin
(74) *Attorney, Agent, or Firm* — Flener IP & Business Law; Zareefa B. Flener

(57) ABSTRACT

The present invention provides a monoclonal antibody that specifically binds to human-derived procalcitonin and application thereof. The present invention also provides a hybridoma cell line secreting the monoclonal antibody and having an accession number of CGMCC No. 10417, and a method for preparing an antibody against procalcitonin by using a procalcitonin mutant antigen as the immunogen.

5 Claims, 3 Drawing Sheets

Specification includes a Sequence Listing.

TB1 M  TB2 TB3

MONOCLONAL ANTIBODY OF HUMAN-DERIVED PROCALCITONIN, AND PREPARATION METHOD AND APPLICATION THEREOF

CROSS-REFERENCE TO RELATED APPLICATION

This application is a continuation application of International patent application No. PCT/CN2016/081545, filed on May 10, 2016, which claims the benefit and priority of Chinese patent application No. CN201510400557.9 filed on Jul. 9, 2015 and CN201510419304.6 filed on Jul. 16, 2015, each of which is incorporated herein by reference in its entirety and for all purposes.

FIELD OF THE INVENTION

The present invention relates to the field of medical diagnosis. In particular, the present invention relates to a hybridoma cell line capable of producing a monoclonal antibody specific for human-derived procalcitonin, and a preparation method thereof. The monoclonal antibody prepared by the hybridoma can be applied to the diagnosis of diseases or related fields.

BACKGROUND OF THE INVENTION

Procalcitonin (PCT), a specific marker for bacterial and fungal infections that was not found until the 1990 s, is a peptide precursor of calcitonin, which has no hormone activity, consists of 116 amino acids, and has a molecular weight of about 13 KD. Procalcitonin can be degraded gradually into aminoprocalcitonin (N-PCT) having 57 amino acids, calcitonin (CT) having 32 amino acids and katacalein having 21 amino acids under the action of enzyme. Procalcitonin is an expression product of calcitonin I gene (CALC-I) on chromosome 11. In the absence of infection, extrathyroidal CALC-I expression is inhibited, and mainly limited to the expression in neuroendocrine cells of thyroid and lung to some extent. Bacterial infection induces CALC-I expression and continuous release of procalcitonin in many types of cells of various tissues all over the body. In recent years, the studies show that procalcitonin is a new indicator having high sensitivity and specificity in the diagnosis of severe systemic bacterial, fungal, parasitic, acute malarial infections, systemic inflammatory responses symptom (SIRS), and multiple organ dysfunction syndrome (MODS).

Procalcitonin consists of 116 amino acids, which can be divided into three fragments depending on domains and functions. The sequence from positions 1 to 57 is N-terminal fragment. Procalcitonin can be cleaved at position 57 from N-terminal in vivo to produce a sequence of amino acids from positions 60 to 116 containing calcitonin. Simultaneously, procalcitonin can also be cleaved by protease at position 91 to form calcitonin and katacalcin (katacalcin of amino acids from positions 96 to 116). Therefore, both the whole procalcitonin and multiple cleaved fragments thereof are present in human serum, and these fragments play a different physiological function in human body as procalcitonin does.

In order to specifically and accurately identify and diagnose the whole procalcitonin fragment, there are three methods for determining the content of procalcitonin. In the first method, an anti-$PCT_{1-57}$ polyclonal antibody is chosen for determining procalcitonin. In the second method, an anti-$PCT_{1-57}$ monoclonal antibody and an anti-$PCT_{60-116}$ monoclonal antibody are chosen for sandwich assay. In the third method, a monoclonal antibody against N-terminal fragment and calcitonin-binding region and an anti-$PCT_{60-116}$ monoclonal antibody are chosen for sandwich assay.

Since the N-terminal of procalcitonin is unstable and is easily degraded, when a pure human-derived procalcitonin antigen is used in immunization, the unstable antigen may generate a weak immune response, which does not meet the preparation conditions of an efficient antibody. Therefore, there is a need in the prior art to solve the problem of a weak immune response due to the unstable antigen when immunized with pure human-derived procalcitonin antigen.

SUMMARY OF THE INVENTION

In order to solve the problem of a weak immune response due to the unstable antigen when immunized with pure human-derived procalcitonin antigen, the present invention intends to provide a monoclonal antibody that specifically binds to a human-derived procalcitonin protein, and a preparation method thereof. The inventors mutated the individual amino acid(s) within the amino acids from positions 1 to 57, mainly the individual amino acid(s) within the amino acids from positions 19 to 40, and accomplished the recombinant expression of the mutated protein in vitro. The inventors found that the above treatment can improve the stability of procalcitonin, which is not easily degraded when injected into the animal after co-emulsification with the adjuvant, resulting in the production of a more efficient antibody. The inventors found by the final epitope analysis that the epitope was the amino acids from positions 20 to 35.

The present invention provides an anti-procalcitonin antibody capable of specifically binding to human-derived procalcitonin, wherein the anti-procalcitonin antibody specifically binds to the same procalcitonin epitope as the anti-procalcitonin monoclonal antibody produced by a hybridoma cell line with an accession number of CGMCC No. 10417.

In one aspect of the present invention, the anti-procalcitonin antibody comprises a humanized sequence of the anti-procalcitonin monoclonal antibody produced by a hybridoma cell line with an accession number of CGMCC No. 10417.

In another aspect of the present invention, the anti-procalcitonin antibody is a monoclonal antibody.

In a further aspect of the present invention, the anti-procalcitonin antibody specifically binds to an epitope having an amino acid sequence of RLLLAALVQDYV (SEQ ID NO: 1).

In one embodiment of the present invention, the anti-procalcitonin antibody is obtained from a hybridoma cell line with an accession number of CGMCC No. 10417.

The present invention also provides an immunodetection reagent comprising the anti-procalcitonin antibody described above, for detection or quantification of procalcitonin or a fragment thereof.

The present invention also provides use of the anti-procalcitonin antibody in the manufacture of an immunodetection reagent for detection or quantification of procalcitonin or a fragment thereof.

The present invention also provides a kit comprising the anti-procalcitonin antibody described above, for detection or quantification of procalcitonin or a fragment thereof. In an embodiment of the present invention, the kit of the present invention comprises at least the anti-procalcitonin antibody described above, and an antibody against an epitope within an amino acid sequence from positions 50 to 116 of procalcitonin; preferably, the antibody against the epitope within the amino acid sequence from positions 50 to 116 of procalcitonin may be an antibody against the epitope within the amino acid sequence from positions 50 to 116 of procalcitonin as disclosed in the prior art. More preferably, the detection or quantification of procalcitonin or a fragment thereof as described in the present invention adopts immunoassay. Furthermore, the immunoassay includes a conventional method in the art, such as chemical method, fluorescence immunoassay, enzyme-linked immunosorbent assay and immunochromatography, etc., the specific assay steps of said assays can be obtained from the prior art.

The present invention also provides use of the anti-procalcitonin antibody in the manufacture of a kit for detection or quantification of procalcitonin or a fragment thereof.

The present invention provides a hybridoma cell line producing an anti-procalcitonin monoclonal antibody, which has an accession number of CGMCC No. 10417.

In addition, the present invention provides a method for preparing an anti-procalcitonin antibody, comprising the following steps of:

(1) mutating the N-terminal amino acid residue(s) of procalcitonin, to obtain a nucleotide sequence corresponding to the sequence of the mutated amino acid residues;

(2) inserting the nucleotide sequence into a prokaryotic expression vector, and carrying out an induction expression and protein purification; and (3) immunizing an animal with the purified protein as immunogen, fusing the splenocytes from the animal with mouse myeloma cells to prepare hybridoma cells, and screening to obtain the hybridoma cells that can stably secrete an anti-procalcitonin antibody, and obtain the corresponding monoclonal antibody.

In an aspect of the present invention, the mutation is carried out to the amino acid residues from positions 1 to 57 of procalcitonin.

In one embodiment of the present invention, the mutated procalcitonin amino acid sequences are SEQ ID NOs: 2-4.

In the present invention, an antibody prepared by the above-described method is also provided.

In one embodiment of the present invention, the antibody is a monoclonal antibody.

The beneficial effects of the present invention are as follows, the human-derived procalcitonin modified by mutation has a higher stability than common antigens, can be used as a calibrator in a kit for quantitatively determining human procalcitonin, and is not easily degraded; and meanwhile is a recombinant protein with a high purity, and can be used as an immunogen and a screening antigen for antibody preparation. In addition, the antibodies produced by the human-derived procalcitonin modified by mutation can not only specifically bind to human-derived procalcitonin, but also have a better titer and a higher specific binding than the existing antibodies against human-derived procalcitonin.

The present invention is further described in more detail by combining the following drawings. As described in detail below, the above aspects and other aspects of the present invention will be apparent.

BRIEF DESCRIPTION OF DEPOSITION

Figure 1:
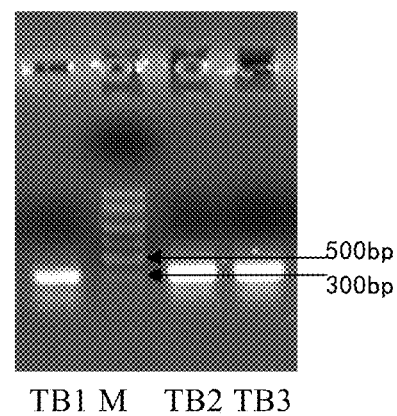
FIG. 1 is the identification results of agarose gel electrophoresis of three mutants. TB1: Mutant 1, M: DL2000 DNA Marker, TB2: Mutant 2, TB3: Mutant 3, wherein the bands indicated by the arrowheads refer to the places of the 500 bp and 300 bp Marker, respectively.

The Balb/c mouse hybridoma cell obtained in the present invention was deposited with an accession number of CGMCC No. 10417 in China General Microbiological Culture Collection Center (CGMCC) on Apr. 1, 2015, CGMCC address: Institute of Microbiology Chinese Academy of Sciences, NO.3 in Court NO.1, Beichen West Road, Chaoyang District, Beijing, Postal code: 100101.

BRIEF DESCRIPTION OF SEQUENCES

The sequences involved in the present invention, including nucleotide sequences and amino acid sequences, have been sorted out to constitute a sequence listing and arranged at the end of the description. In addition, the inventor has submitted a computer readable form file of the sequence listing.

DEPOSIT OF MICROORGANISM

The Balb/c mouse hybridoma cell was deposited as CGMCC Accession No.:10417 on Apr. 1, 2015 with the China General Microbiological Culture Collection Center (CGMCC), Institute of Microbiology Chinese Academy of Sciences, NO.3 in Court NO.1, Beichen West Road, Chaoyang District, Beijing, Postal code: 100101. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by CGMCC under the terms of the Budapest Treaty, and subject to an agreement between Applicant and CGMCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited strain is not to be construed as a license to practice the invention in contravention of the rights granted under the authority of any government in accordance with its patent laws.

DETAILED DESCRIPTION OF THE INVENTION

The present invention is not limited to the specific methodology, solutions, antibodies or cell lines described herein, since they may vary. In addition, the terms used herein are only used for the purpose of describing the specific embodiments, rather than limiting the scope of the present invention.

Unless otherwise defined herein, all the technical and scientific terms and any abbreviations herein have the same meanings as generally understood by one skilled in the art to which the present invention pertains. Although in the practicing of the present invention, methods and materials similar or equivalent to those described herein may be used, the exemplified methods, apparatuses and materials are described herein.

Unless otherwise specified, the terms of the present invention have the meanings generally used in the art.

The term "antibody" used in the present invention, refers to any immunoglobulin or whole molecule binding to a specific epitope, and a fragment thereof. The antibody includes, but is not limited to, a polyclonal antibody, a monoclonal antibody, a chimeric antibody, a humanized antibody, a single-chain antibody and a fragment and/or a part of whole antibody, as long as these fragments or parts retain the antigen binding ability of the parent antibody. For example, in the present invention, "anti-procalcitonin antibody" refers to a monoclonal antibody, a polyclonal antibody, a single-chain antibody, and a fragment or a part thereof having immunological activity, which can specifically bind to procalcitonin protein or a functional variant or functional fragment thereof. In the present invention, the terms such as "procalcitonin antibody", "anti-procalcitonin antibody" and "antibody against procalcitonin" can be used interchangeably.

The term "bind (binding)" or "specifically bind (specific binding)" used in the present invention refers to the binding of an antibody to an epitope of an antigen as measured in in vitro assay using a purified wild-type antigen, preferably in plasmon resonance measurement(BIAcore, GE-Healthcare Uppsala, Sweden). The binding affinity is defined by the terms ka (binding rate constant of the antibody from an antibody/antigen complex), kD (dissociation constant) and KD (kD/ka). The term "bind (binding)" or "specifically bind (specific binding)" refers to a binding affinity (KD) of $10^{-8}$ mol/l or less, preferably of $10^{-9}$ to $10^{-13}$ mol/l. Thus, the procalcitonin antibody of the present invention may specifically bind to an antigen with a binding affinity (Kd) of $10^{-8}$ mol/l or less, preferably of $10^{-9}$ to $10^{-13}$ mol/l.

The term "human monoclonal antibody" used in the present invention refers to an antibody displaying a single binding specificity which has variable and constant regions derived from human germline immunoglobulin sequences. In one embodiment, the human monoclonal antibody is produced by a hybridoma which includes a B cell obtained from a transgenic non-human animal, e.g. a transgenic mouse, having a genome comprising a human heavy chain transgene and a light human chain transgene, fused to an immortalized cell.

EXAMPLES

Example 1

1 Construction of Procalcitonin Mutant Plasmid as Well as Expression and Purification of Recombinant Protein 1.1 Experimental Materials 1.1.1 Bacterial Strain and Plasmid E. coli Top10, BL21(DE3)

Plasmid pET34

1.1.2 Primers

```
Mutation strategy:
Mutant 1:
                                        (SEQ ID NO: 2)
APFRSALESSPADPATLSEEEARLLLAALVQDYVQMKASELEQEQEREGS
SLDSPRSKRCGNLSTCMLGTYTQDFNKFHTFPQTAIGVGAPGKKRDMSSD
LERDHRPHVSMPQNAN Mutant 2:
                                        (SEQ ID NO: 3)
APFRSALESSPADPATLSEDEARLLLAALVQDYVQMKAAELEQEQEREGS
SLDSPRSKRCGNLSTCMLGTYTQDFNKFHTFPQTAIGVGAPGKKRDMSSD
LERDHRPHVSMPQNAN Mutant 3:
                                        (SEQ ID NO: 4)
APFRSALESSPADPATLAEDEARLLLAALVQDYVQMKASELEQEQEREGS
SLDSPRSKRCGNLSTCMLGTYTQDFNKFHTFPQTAIGVGAPGKKRDMSSD
LERDHRPHVSMPQNAN Whole gene synthesis:
Mutant 1:
                                        (SEQ ID NO: 5)
CACGGATCCGCACCGTTCCGTTCTGCGCTGGAAAGCTCTCCAGCCGATCC

GGCCACCCTGAGCGAAGAGGAAGCGCGTCTGCTGCTGGCGGCACTGGTCC

AGGACTACGTTCAGATGAAAGCGTCTGAACTGGAGCAGGAACAGGAACGC

GAAGGTAGCAGCCTGGACTCTCCACGTTCCAAGCGCTGTGGTAACCTGAG

CACTTGTATGCTGGGCACCTATACTCAGGACTTCAACAAGTTCCACACTT

TCCCGCAGACTGCGATCGGTGTGGGCGCACCGGGTAAGAAACGTGACATG

AGCTCCGACCTGGAGCGTGACCACCGTCCACATGTATCCATGCCACAGAA

CGCCAACTAACTCGAGCAC

Mutant 2:
                                        (SEQ ID NO: 6)
CACGGATCCGCTCCGTTCCGCAGCGCACTGGAGTCCTCTCCAGCCGACCC

TGCTACCCTGTCTGAAGACGAAGCGCGTCTGCTGCTGGCTGCGCTGGTTC

AGGACTACGTACAGATGAAGGCGGCTGAACTGGAACAAGAACAGGAGCGC

GAAGGCTCCAGCCTGGATTCCCCGCGTAGCAAACGCTGTGGCAACCTGTC

CACTTGCATGCTGGGTACCTACACCCAAGACTTTAACAAATTTCACACGT

TTCCGCAAACTGCTATTGGCGTTGGTGCCCCGGGTAAGAAACGTGATATG

TCTAGCGACCTGGAACGCGATCACCGCCCGCACGTTAGCATGCCGCAGAA

CGCAAATTAACTCGAGCAC

Mutant 3:
                                        (SEQ ID NO: 7)
CACGGATCCGCACCATTTCGTTCTGCTCTGGAATCTTCTCCTGCTGATCC

TGCAACCCTGGCTGAAGACGAGGCGCGTCTGCTGCTGGCAGCACTGGTTC

AGGATTATGTTCAGATGAAAGCGAGCGAACTGGAGCAGGAACAGGAGCGC

GAGGGCAGCTCTCTGGATTCTCCTCGTAGCAAACGTTGCGGTAACCTGAG

CACCTGCATGCTGGGTACCTACACGCAAGACTTCAACAAATTCCACACTT

TTCCGCAGACTGCGATTGGTGTGGGTGCGCCGGGTAAAAAGCGTGACATG

AGCTCTGACCTGGAACGTGACCATCGTCCGCATGTTTCTATGCCGCAGAA

CGCGAACTAACTCGAGCAC
```

Primer design:
Mutant 1:
PCT-TB1-1:
(SEQ ID NO: 8)
CACGGATCCGCACCGTTCCGTTCTGCGCTGG

PCT-TB1-2:
(SEQ ID NO: 9)
TGGCCGGATCGGCTGGAGAGCTTTCCAGCGCAGAACGGAAC

PCT-TB1-3:
(SEQ ID NO: 10)
CAGCCGATCCGGCCACCCTGAGCGAAGAGGAAGCGCGTCTG

PCT-TB1-4:
(SEQ ID NO: 11)
TCCTGGACCAGTGCCGCCAGCAGCAGACGCGCTTCCTCTTC

PCT-TB1-5:
(SEQ ID NO: 12)
CGGCACTGGTCCAGGACTACGTTCAGATGAAAGCGTCTGAA

PCT-TB1-6:
(SEQ ID NO: 13)
GTTCCTGTTCCTGCTCCAGTTCAGACGCTTTCATCTGAACG

PCT-TB1-7:
(SEQ ID NO: 14)
CTGGAGCAGGAACAGGAACGCGAAGGTAGCAGCCTGGACTC

PCT-TB1-8:
(SEQ ID NO: 15)
TACCACAGCGCTTGGAACGTGGAGAGTCCAGGCTGCTACCT

PCT-TB1-9:
(SEQ ID NO: 16)
GTTCCAAGCGCTGTGGTAACCTGAGCACTTGTATGCTGGGC

PCT-TB1-10:
(SEQ ID NO: 17)
TTGTTGAAGTCCTGAGTATAGGTGCCCAGCATACAAGTGCT

PCT-TB1-11:
(SEQ ID NO: 18)
ACCTATACTCAGGACTTCAACAAGTTCCACACTTTCCCGCA

PCT-TB1-12:
(SEQ ID NO: 19)
GTGCGCCCACACCGATCGCAGTCTGCGGGAAAGTGTGGAAC

PCT-TB1-13:
(SEQ ID NO: 20)
TCGGTGTGGGCGCACCGGGTAAGAAACGTGACATGAGCTCC

PCT-TB1-14:
(SEQ ID NO: 21)
CGGTGGTCACGCTCCAGGTCGGAGCTCATGTCACGTTTCTT

PCT-TB1-15:
(SEQ ID NO: 22)
TGGAGCGTGACCACCGTCCACATGTATCCATGCCACAGAAC

PCT-TB1-16:
(SEQ ID NO: 23)
GTGCTCGAGTTAGTTGGCGTTCTGTGGCATGGATACATG

Mutant 2:
PCT-TB2-1:
(SEQ ID NO: 24)
CACGGATCCGCTCCGTTCCGCAGCGCACTG

PCT-TB2-2:
(SEQ ID NO: 25)
TAGCAGGGTCGGCTGGAGAGGACTCCAGTGCGCTGCGGAAC

PCT-TB2-3:
(SEQ ID NO: 26)
CCAGCCGACCCTGCTACCCTGTCTGAAGACGAAGCGCGTCT

PCT-TB2-4:
(SEQ ID NO: 27)
CCTGAACCAGCGCAGCCAGCAGCAGACGCGCTTCGTCTTCA

PCT-TB2-5:
(SEQ ID NO: 28)
GCTGCGCTGGTTCAGGACTACGTACAGATGAAGGCGGCTGA

PCT-TB2-6:
(SEQ ID NO: 29)
CGCGCTCCTGTTCTTGTTCCAGTTCAGCCGCCTTCATCTGT

PCT-TB2-7:
(SEQ ID NO: 30)
AACAAGAACAGGAGCGCGAAGGCTCCAGCCTGGATTCCCCG

PCT-TB2-8:
(SEQ ID NO: 31)
CAGGTTGCCACAGCGTTTGCTACGCGGGGAATCCAGGCTGG

PCT-TB2-9:
(SEQ ID NO: 32)
AACGCTGTGGCAACCTGTCCACTTGCATGCTGGGTACCTAC

PCT-TB2-10:
(SEQ ID NO: 33)
GTGAAATTTGTTAAAGTCTTGGGTGTAGGTACCCAGCATGCAAG

PCT-TB2-11:
(SEQ ID NO: 34)
ACCCAAGACTTTAACAAATTTCACACGTTTCCGCAAACTGCTA

PCT-TB2-12:
(SEQ ID NO: 35)
TTACCCGGGGCACCAACGCCAATAGCAGTTTGCGGAAACGT

PCT-TB2-13:
(SEQ ID NO: 36)
GTTGGTGCCCCGGGTAAGAAACGTGATATGTCTAGCGACCT

PCT-TB2-14:
(SEQ ID NO: 37)
GCGGGCGGTGATCGCGTTCCAGGTCGCTAGACATATCACGT

PCT-TB2-15:
(SEQ ID NO: 38)
GCGATCACCGCCCGCACGTTAGCATGCCGCAGAACGCAAAT

PCT-TB2-16:
(SEQ ID NO: 39)
GTGCTCGAGTTAATTTGCGTTCTGCGGCA

Mutant 3:
PCT-TB3-1:
(SEQ ID NO: 40)
CACGGATCCGCACCATTTCGTTCTGCTCTGGAATCT

PCT-TB3-2:
(SEQ ID NO: 41)
GTTGCAGGATCAGCAGGAGAAGATTCCAGAGCAGAACGAAA

PCT-TB3-3:
(SEQ ID NO: 42)
CTCCTGCTGATCCTGCAACCCTGGCTGAAGACGAGGCGCGT

PCT-TB3-4:
(SEQ ID NO: 43)
CCTGAACCAGTGCTGCCAGCAGCAGACGCGCCTCGTCTTCA

PCT-TB3-5:
(SEQ ID NO: 44)
GGCAGCACTGGTTCAGGATTATGTTCAGATGAAAGCGAGCG

PCT-TB3-6:
(SEQ ID NO: 45)
GCTCCTGTTCCTGCTCCAGTTCGCTCGCTTTCATCTGAACA

PCT-TB3-7:
(SEQ ID NO: 46)
TGGAGCAGGAACAGGAGCGCGAGGGCAGCTCTCTGGATTCT

-continued

PCT-TB3-8:
(SEQ ID NO: 47)
TACCGCAACGTTTGCTACGAGGAGAATCCAGAGAGCTGCCC

PCT-TB3-9:
(SEQ ID NO: 48)
CGTAGCAAACGTTGCGGTAACCTGAGCACCTGCATGCTGGG

PCT-TB3-10:
(SEQ ID NO: 49)
TTTGTTGAAGTCTTGCGTGTAGGTACCCAGCATGCAGGTGC

PCT-TB3-11:
(SEQ ID NO: 50)
CTACACGCAAGACTTCAACAAATTCCACACTTTTCCGCAGAC

PCT-TB3-12:
(SEQ ID NO: 51)
GGCGCACCCACACCAATCGCAGTCTGCGGAAAAGTGTGGAA

PCT-TB3-13:
(SEQ ID NO: 52)
TGGTGTGGGTGCGCCGGGTAAAAAGCGTGACATGAGCTCTG

PCT-TB3-14:
(SEQ ID NO: 53)
GGACGATGGTCACGTTCCAGGTCAGAGCTCATGTCACGCTT

PCT-TB3-15:
(SEQ ID NO: 54)
GGAACGTGACCATCGTCCGCATGTTTCTATGCCGCAGAACG

PCT-TB3-16:
(SEQ ID NO: 55)
GTGCTCGAGTTAGTTCGCGTTCTGCGGCATAGAAACA

1.1.3 Main Reagents and Preparation

Restrictive endonuclease BamH I, Xho I, Fast pfu DNA polymerase, and Taq polymerase were purchased from Takara Company; T4-DNA ligase was purchased from Promega Company; ampicillin antibiotic was purchased from Sangon Biotech (Shanghai) Co., Ltd.; DL2000 DNA Marker was purchased from GenScript Co., Ltd.; Agarose gel DNA Extraction Kit was purchased from Tiangen Biotech Co., Ltd.; Plasmid Extraction Kit was purchased from Axygen Company; Tryptone and Yeast extract were OXOID products; IPTG and protein Marker were purchased from Sun-Shine Biotechnology Co., LTD.; Ni column gel (Ni-Sepharose 6 FF) was purchased from GE Company.

Buffer A: 20 mM Tris, 300 mM NaCl, 20 mM Imi, pH 7.4
Buffer B: 20 mM Tris, 300 mM NaCl, 80 mM Imi, pH 7.4
Buffer C: 20 mM Tris, 300 mM NaCl, 250 mM Imi, pH 7.4

1.1.4 Main Experimental Apparatus
1) Refrigerated centrifuge
2) Desk centrifuge
3) PCR instrument
4) Nucleic acid electrophoresis apparatus
5) Protein electrophoresis apparatus
6) Gel imaging analyzer
7) Ultrasonic cell disruptor
8) Thermostatic culture shaker

1.2 Experimental Methods

1.2.1 Obtainment of the Target Gene

By overlap-extension PCR, 16 primers were linked, respectively, resulting in the full length of three mutants. Agarose gel identification (see FIG. 1) was performed, the PCR product was purified by using an Agarose gel DNA Extraction Kit.

1.2.2 Double Enzyme Digestion of Plasmid and PCR Product

1) Enzyme Digestion of three PCR Products

| | |
|---|---|
| PCR product | 15 µl |
| Enzyme digestion buffer | 3 µl |
| BamH I | 2 µl |
| Xho I | 2 µl |
| ddH$_2$O | 8 µl |

2) Enzyme Digestion of Plasmid pET34

| | |
|---|---|
| Plasmid pET34 | 8 µl |
| Enzyme digestion buffer | 3 µl |
| BamH I | 2 µl |
| Xho I | 2 µl |
| ddH$_2$O | 15 µl |

Figure 2:
FIG. 2 is the identification results of agarose gel electrophoresis of dual-enzyme digested pET34.

Said reaction solutions were mixed homogeneously, respectively, and after reaction at 37° C. for 30 min, the identification was performed by electrophoresis (see FIG. 2). After complete enzyme digestion, the purification was performed in accordance with the instructions of DNA Fragment Purification Kit.

1.2.3 Ligation Reaction

As calculated by DNA ligation reaction calculator, the PCR product was reacted with a carrier DNA at a molar ratio of 9:1, and under the action of T4-DNA ligase, the ligation was performed at 22° C. for 30 min.

1.2.4 Transformation

10 µl the ligation product was added to 100 µl Top10 competent cells. The mixture was blown with a pipette tip for several times, placed in ice bath for 30 min, subjected to thermal shock at 42° C. for 90 s, placed in ice bath again for 2 min, and added with 800 µl LB culture medium. After incubation at 37° C. in a shaker for 1 h, the centrifugation was performed at 6000 rpm for 30 s, and about 800 µl supernatant was removed. The bacteria cells were re-suspended and spread onto LB plate with ampicillin.

1.2.5 Bacteria Liquid PCR

The next day, the individual bacterial colonies were selected after bacteria grew out.

Mutation 1:

| | |
|---|---|
| ddH$_2$O | 20.7 µl |
| buffer | 3 µl |
| dNTP | 1 µl |
| Primer PCT-TB1-1 | 1 µl |
| Primer PCT-TB1-16 | 1 µl |
| Bacteria liquid | 3 µl |
| Taq polymerase | 0.3 µl |

Mutation 2:

| | |
|---|---|
| ddH$_2$O | 20.7 µl |
| buffer | 3 µl |
| dNTP | 1 µl |
| Primer PCT-TB2-1 | 1 µl |
| Primer PCT-TB2-16 | 1 µl |
| Bacteria liquid | 3 µl |
| Taq polymerase | 0.3 µl |

Mutation 3:

| | |
|---|---|
| ddH₂O | 20.7 μl |
| buffer | 3 μl |
| dNTP | 1 μl |
| Primer PCT-TB3-1 | 1 μl |
| Primer PCT-TB3-16 | 1 μl |
| Bacteria liquid | 3 μl |
| Taq polymerase | 0.3 μl |

Figure 3:
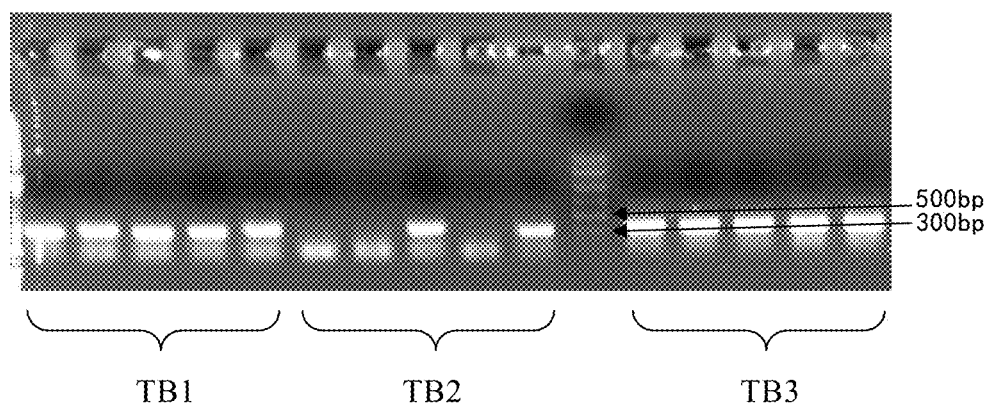
FIG. 3 is the identification results of agarose gel electrophoresis of bacteria liquid PCR. TB1: Mutant 1, TB2: Mutant 2, TB3: Mutant 3, wherein the bands indicated by the arrowheads refer to the places of the 500bp and 300bp Marker, respectively.

PCR conditions: 95° C., 3 min. 95° C., 30 s, 58° C., 30 s, 72° C., 30 s. 30 cycles. 8 μl sample was verified by agarose gel electrophoresis (see FIG. 3).

1.2.6 Plasmid Extraction

Figure 4:
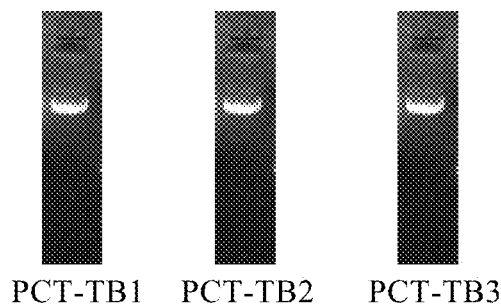
FIG. 4 is the identification results of agarose gel electrophoresis of the extracted plasmids pET34-PCT-TB1, pET34-PCT-TB2, and pET34-PCT-TB3.

The extraction of plasmids pET34-PCT-TB1, pET34-PCT-TB2 and pET34-PCT-TB3 were performed in accordance with the instructions of the kit, and 2 μl sample was verified by agarose gel electrophoresis (see FIG. 4).

1.2.7 Sequencing

The extracted plasmids pET34-PCT-TB1, pET34-PCT-TB2 and pET34-PCT-TB3 were sent to GenScript Company for sequencing. The sequencing results were in accordance with the designed sequences.

1.2.8 Re-Transformation

The BL21(DE3) competent cells were separately transformed with the recombinant plasmids pET34-PCT-TB1, pET34-PCT-TB2 and pET34-PCT-TB3, which were verified by sequencing to have the correct sequences.

1.2.9 Expression

1) Activation: individual bacterial colonies containing pET34-PCT-TB1, pET34-PCT-TB2, pET34-PCT-TB3, were picked and cultured in 3 ml LB culture medium overnight.

2) Amplification culture and induction expression: to 100 ml LB liquid culture medium, 1 ml the activated bacteria liquid was added to perform amplification culture; after shaking at 37° C., 200 rpm for 2-3 h, the absorbance value $OD_{600}$ of the bacteria was measured. When $A_{600\,nm}$ reached 0.4~0.6, 1 mol/L IPTG solution was added until its final concentration was 1 mmol/L. After induction expression for 4 h, the bacteria were harvested.

1.2.10 Protein Purification

Figure 5:
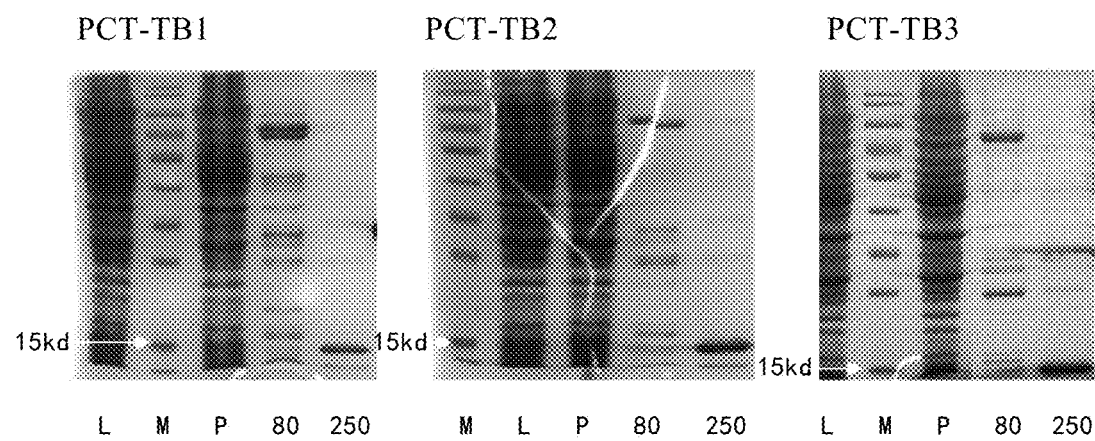
FIG. 5 is the identification results of SDS-PAGE electrophoresis of the purified pET34-PCT-TB1, pET34-PCT-TB2, and pET34-PCT-TB3 protein. The band indicated by the arrowhead is a protein band of 15 kd. L: Loading, M: protein Marker, P: filtered liquid, 80: 80 mM imidazole, 250: 250 mM imidazole.

The bacteria were collected by centrifugation at 12000 rpm, and the bacteria were re-suspended in 20 ml Buffer A, after ultrasonation in ice bath for 20 min and centrifugation at 12000 rpm for 20 min, the supernatant was taken, purified by passing through a Ni column, prewashed by Buffer A and Buffer B, and the target protein was eluted with Buffer C, dialyzed into PBS, 20 μl the dialyzed sample was identified by SDS-PAGE electrophoresis (see FIG. 5).

Example 2

Preparation of Hybridoma Cell Line 2.1 Immunization of Mice

Three 6-week old Balb/c mice were used. After Freund's adjuvant and an antigen were mixed and emulsified, the resultant mixture was subcutaneously injected to the back of mice for immunization three times with an interval of 2 weeks. After the completion of immunization, blood was collected from the orbits of mice for determining titer. The mice, the titer of which met the requirement, were directly injected with the antigen intraperitoneally, and were prepared for use three days after the boost immunization.

2.2 SP2/0 Myeloma Cell Culture

To an incomplete DMEM medium, 10% fetal bovine serum and 1% double antibody were added, to prepare a complete DMEM medium. 15 ml the complete medium was added to a T75 cell culture flask, in which SP2/0 myeloma cells were cultured. The medium was replaced every two days. When the cells were in exponential phase and the cells spread to 70% of the bottom of the flask, the medium was replaced, and the cells were prepared for use the next day.

2.3 Cell Fusion

The spleen of the standby mice was ground in a 200 mesh sterile sieve, and was blown and washed with incomplete DMEM medium. The suspension was transferred to a 50 ml sterile centrifuge tube and mixed homogeneously, and the cells were then counted. SP2/0 culture supernatant was discarded, and the cells were blown off with incomplete DMEM medium, and transferred to a 50 ml sterile centrifuge tube and mixed homogenously, and then counted. The spleen cells and the myeloma cells were mixed at a ratio of 5:1, and centrifuged at 1500 rpm for 3 min, the supernatant was discarded. After mixing homogeneously by flapping, in 37° C. water bath, 1 ml 50% PEG 1500 was added within 1 min, and after standing for 1.5 min, 40 ml incomplete DMEM medium was added to stop the reaction. After centrifugation at 1000 rpm for 10 min, the supernatant was discarded. After mixing homogeneously by flapping, the cells were washed again and centrifuged as described above. The supernatant was discarded. The cells were re-suspended in HAT culture medium (complete DMEM medium+HAT solution) and mixed homogeneously, and then spread onto 96-well cell culture plate, at 100 μl/well.

Example 3

Screening of Hybridoma Cell Line 3.1 Detection of Culture Supernatant

At the seventh day of fusion, a half of the medium in the fusion well was replaced by HT culture medium (complete DMEM medium+HT solution). The supernatant was taken for detection three days later, at 60 μl/well. The $OD_{450}$ value of the supernatant was measured by indirect ELISA, and the wells, which had a measured value above 2.5 fold of the value of the control well, were used as positive wells and were marked for later use.

3.2 Cell Subclone

The marked positive wells were blown with a pasteurpipette, and after mixing homogeneously, a small amount was taken for counting. 200-500 cells were taken for limiting dilution with complete DMEM medium, and spread onto the 96-well cell culture plate containing feeder layer cells, at 200 μl/well. The first subcloning was finished. 5-7 days later, the supernatant was taken and detected, and a monoclonal cell stack was chosen to carry out the second subcloning. The operation was repeated until the whole culture plate (containing cells) of the screened hybridoma cells were positive twice, and the cells were obtained from the subclones of the monoclonal cells. The subcloning was stopped, and the finally obtained monoclonal cells were selected and cultured in 24-well cell culture plate, for amplification culture and cryopreservation.

3.3 Cryopreservation of Cells

When the hybridoma cells in the 24-well plate spread to 80% of the bottom of the flask, the cells were transferred to a cell culture flask after blowing homogeneously with a pasteurpipette. When the cells spread to 80% of the bottom of the flask, the cells were cryopreserved. The cells in the flask were blown off and transferred to a 50 ml sterile centrifuge tube, and a small amount was taken for counting. The remaining cells were centrifuged at 1500 rpm for 3 min. The supernatant was discarded. After mixing homogeneously by flapping, cryopreservation liquid (90% fetal bovine serum+10% DMSO) was added to prepare a cell suspension ($1\times10^6$ cells/ml) and was sub-packaged into 2 ml cryopreservation tubes at 1 ml/tube. The tubes were placed in a cell freezing container at −70° C. overnight, and transferred to liquid nitrogen the next day for storage.

Example 4

Preparation of Monoclonal Antibodies 4.1 Hybridoma Cell Resuscitation and Culture The desired hybridoma cells were taken from liquid nitrogen, and the freezing tube was quickly placed in 37° C. water bath, and was shaken back and forth to promote quick thawing. The cells were completely thawed within 1 min, and centrifuged at 1500 rpm for 3 min. The supernatant was discarded, and the cells was re-suspended in complete DMEM medium and transferred to a cell culture flask and cultured. The resuscitation was finished. If live cells were observed under a microscope, the resuscitation was successful. Otherwise, the resuscitation was required to be done again.

The next day, the medium was replaced with fresh culture medium, and later the medium was replaced every two days. When the cells spread to 70% of the bottom of the flask, the cells were blown off with complete DMEM medium. A half of the cells were transferred to a new culture flask, and cultured in the fresh culture medium supplemented. The cells in the original flask were cultured continuously by supplementing medium. The amplification culture was performed in such a manner until the desired number of cells was achieved.

4.2 Preparation of Ascites Antibody

When the cells spread to 80% of the bottom of the flask, the cells in the flask were blown washed with sterile PBS solution, collected in a 50 ml sterile centrifuge tube, and centrifuged at 1500 rpm for 3 min. The supernatant was discarded. The cells were re-suspended in PBS, and centrifuged again after mixing homogenously. The supernatant was discarded. The cells were re-suspended in PBS to prepare a cell suspension at $2\times10^6$ cells/ml for later use.

Three days before collecting cells, 6-8 week old Balb/c male mice were intraperitoneally injected with sterile paraffin oil, at 0.5 ml/mouse, for later use.

The standby mice were intraperitoneally injected with said cell suspension, at 0.5 ml/mouse.

5 days later, ascites was produced in the mice, and the ascites was collected in a centrifuge tube at the end of a 20 ml syringe needle which was inserted into the peritoneal cavity of the mice. When no ascites dripped, the needle was pulled out, and the mice were put back. The ascites was taken every other day. The operation was repeated until the mice died.

The collected ascites was stored in the presence of a preservative at 4° C. When the collection of ascites was finished, the ascites was mixed homogeneously, and the ascites antibody was purified.

4.3 Purification of Ascites Antibody

To the ascites of the mice, an equal volume of a binding buffer was added. After mixing homogeneously, the obtained mixture was subjected to standing for 1 h at 4° C., and centrifuged (4° C., 12000 rpm, 20 min), the supernatant was taken and subjected to suction filtration through a 0.45 μm membrane to remove the particulate matter.

After the suction filtration, the ascites was loaded onto a protein A affinity chromatographic column pre-equilibrated with a binding buffer, wherein the flow rate was controlled at 2 mL/min.

After the loading, the column was washed with binding buffer until no protein flew out.

The column was eluted with pH 3.0 eluent, and the fraction with a high protein content, i.e., the purified monoclonal antibody, was collected in a centrifuge tube in which a neutralizing buffer has been added. After dialysis with PBS, the antibody was determined for its immunological activity, and the antibody was stored in the presence of preservative, for later use.

After the antibody was collected, the chromatographic column was regenerated with 3 column volume of regeneration buffer, washed with 20% ethanol, and stored in a 4° C. refrigerator.

Binding Buffer: 0.1 M Gly, pH9.0, containing 3 M NaCl;

Eluting Buffer: 0.1 M Gly, pH3.0, containing 0.15 M NaCl;

Regeneration Buffer: 0.1 M Gly, pH2.0, containing 0.15 M NaCl;

Neutralizing Buffer: 1 M Tris-HCl, pH8.0, containing 0.15 M NaCl 4.4 Titer of Monoclonal Antibody The antibody titer was determined by indirect ELISA. The purified antibody was taken and diluted in a gradient from $10^{-4}$ to $10^{-7}$. Three parallel wells were set for each concentration. Antigen coating: the corresponding antigen was diluted with a coating solution (carbonate buffer pH9.6, 0.05 mol/L) to 2 ug/ml, added to a 96-well ELISA plate, at 100 μl/well, incubated at 4° C. overnight (or incubated at 37° C. for 1 h), washed three times, and patted dry.

Blocking: blocked with 1% BSA, at 200 μl/well, incubated at 37° C. for 1 h, washed three times, and patted dry.

Adding an antibody to be tested: the diluted antibody was added to the plate wells, at 100 μl/well, and incubated at 37° C. for 1 h (or at 4° C. overnight), washed three times, and patted dry.

Adding enzyme-labeled second antibody: goat anti-mouse IgG-HRP was added, a suitable dilution concentration of which was determined by chequerboard titration, at 100 μl/well, incubated at 37° C. for 1 h, washed three times, and patted dry.

Coloration: TMB color liquid was placed in a 37° C. constant temperature incubator under protection from light, at 100 μl/well, and incubated at 37° C. for 10~15 min.

Stopping the reaction: 50 μl of 2 mol/L sulfuric acid was added to each well to stop the reaction.

Determination of OD value at 450 nm: the OD value was determined by an ELISA instrument, the value of the blank well was regarded as zero; if the OD value in the well to be tested was greater than 0.2 and above 2.1 fold of the value of the negative control well, the well was regarded as positive; the corresponding antibody dilution factor of the minimum determined value was used as the titer of the antibody, and when the OD value was close to 1.0, the antibody dilution was the best antibody dilution.

The titer determination results are as follows:

TABLE 1

| Antibody dilutability | OD450 | | |
|---|---|---|---|
| | 1 | 2 | 3 |
| $10^{-4}$ | 3.024 | 3.198 | 3.083 |
| $10^{-5}$ | 2.179 | 2.334 | 2.546 |
| $10^{-6}$ | 1.136 | 1.279 | 1.204 |
| $10^{-7}$ | 0.262 | 0.204 | 0.217 |
| Blank | 0.098 | 0.168 | 0.087 |

A person skilled in the art shall understand that although for the purpose of exemplification and illustration, the embodiments of the present invention are described herein, various modifications may be made thereto without departing from the spirit and scope of the present invention. Therefore, the embodiments and examples of the present invention shall not be regarded as limiting the present invention. The present invention is defined only by the attached claims.

The invention claimed is:

1. An anti-procalcitonin antibody capable of specifically binding to human-derived procalcitonin, wherein the anti-procalcitonin antibody is anti-procalcitonin monoclonal antibody produced by the hybridoma cell line identified by Accession Number CGMCC No. 10417.

2. The anti-procalcitonin antibody according to claim 1, wherein the anti-procalcitonin antibody specifically binds to an epitope having the amino acid sequence of SEQ ID NO: 1.

3. An immunodetection reagent or kit for the detection or quantification of procalcitonin or a fragment thereof, the reagent or kit comprising the anti-procalcitonin antibody of claim 1.

4. The immunodetection reagent or kit according to claim 3, wherein the anti-procalcitonin antibody specifically binds to an epitope having the amino acid sequence of SEQ ID NO: 1.

5. A hybridoma cell line identified by Accession Number CGMCC No. 10417.

* * * * *

SEQUENCE LISTING

<160> NUMBER OF SEQ ID NOS: 55

<210> SEQ ID NO 1
<211> LENGTH: 12
<212> TYPE: PRT
<213> ORGANISM: Homo sapiens

<400> SEQUENCE: 1

Arg Leu Leu Leu Ala Ala Leu Val Gln Asp Tyr Val
1               5                   10

<210> SEQ ID NO 2
<211> LENGTH: 116
<212> TYPE: PRT
<213> ORGANISM: Homo sapiens

<400> SEQUENCE: 2

Ala Pro Phe Arg Ser Ala Leu Glu Ser Ser Pro Ala Asp Pro Ala Thr
1               5                   10                  15

Leu Ser Glu Glu Glu Ala Arg Leu Leu Leu Ala Ala Leu Val Gln Asp
            20                  25                  30

Tyr Val Gln Met Lys Ala Ser Glu Leu Glu Gln Glu Gln Glu Arg Glu
        35                  40                  45

Gly Ser Ser Leu Asp Ser Pro Arg Ser Lys Arg Cys Gly Asn Leu Ser
    50                  55                  60

Thr Cys Met Leu Gly Thr Tyr Thr Gln Asp Phe Asn Lys Phe His Thr
65                  70                  75                  80

Phe Pro Gln Thr Ala Ile Gly Val Gly Ala Pro Gly Lys Lys Arg Asp
                85                  90                  95

Met Ser Ser Asp Leu Glu Arg Asp His Arg Pro His Val Ser Met Pro
                100                 105                 110

Gln Asn Ala Asn
        115

<210> SEQ ID NO 3
<211> LENGTH: 116
<212> TYPE: PRT
<213> ORGANISM: Homo sapiens

<400> SEQUENCE: 3

Ala Pro Phe Arg Ser Ala Leu Glu Ser Ser Pro Ala Asp Pro Ala Thr
1               5                   10                  15

Leu Ser Glu Asp Glu Ala Arg Leu Leu Leu Ala Ala Leu Val Gln Asp
            20                  25                  30

Tyr Val Gln Met Lys Ala Ala Glu Leu Glu Gln Glu Gln Glu Arg Glu
        35                  40                  45

Gly Ser Ser Leu Asp Ser Pro Arg Ser Lys Arg Cys Gly Asn Leu Ser
    50                  55                  60

Thr Cys Met Leu Gly Thr Tyr Thr Gln Asp Phe Asn Lys Phe His Thr
65                  70                  75                  80

Phe Pro Gln Thr Ala Ile Gly Val Gly Ala Pro Gly Lys Lys Arg Asp
                85                  90                  95

Met Ser Ser Asp Leu Glu Arg Asp His Arg Pro His Val Ser Met Pro
            100                 105                 110

Gln Asn Ala Asn
        115

<210> SEQ ID NO 4
<211> LENGTH: 116
<212> TYPE: PRT
<213> ORGANISM: Homo sapiens

<400> SEQUENCE: 4

Ala Pro Phe Arg Ser Ala Leu Glu Ser Ser Pro Ala Asp Pro Ala Thr
1               5                   10                  15

Leu Ala Glu Asp Glu Ala Arg Leu Leu Leu Ala Ala Leu Val Gln Asp
            20                  25                  30

Tyr Val Gln Met Lys Ala Ser Glu Leu Glu Gln Glu Gln Glu Arg Glu
        35                  40                  45

Gly Ser Ser Leu Asp Ser Pro Arg Ser Lys Arg Cys Gly Asn Leu Ser
    50                  55                  60

Thr Cys Met Leu Gly Thr Tyr Thr Gln Asp Phe Asn Lys Phe His Thr
65                  70                  75                  80

Phe Pro Gln Thr Ala Ile Gly Val Gly Ala Pro Gly Lys Lys Arg Asp
                85                  90                  95

Met Ser Ser Asp Leu Glu Arg Asp His Arg Pro His Val Ser Met Pro
            100                 105                 110

Gln Asn Ala Asn
        115

<210> SEQ ID NO 5
<211> LENGTH: 369
<212> TYPE: DNA
<213> ORGANISM: Homo sapiens

<400> SEQUENCE: 5
cacggatccg caccgttccg ttctgcgctg gaaagctctc cagccgatcc ggccaccctg      60
agcgaagagg aagcgcgtct gctgctggcg gcactggtcc aggactacgt tcagatgaaa     120
gcgtctgaac tggagcagga acaggaacgc gaaggtagca gcctggactc tccacgttcc     180
aagcgctgtg gtaacctgag cacttgtatg ctgggcacct atactcagga cttcaacaag     240
ttccacactt tcccgcagac tgcgatcggt gtgggcgcac cggtaagaa acgtgacatg     300 agctccgacc tggagcgtga ccaccgtcca catgtatcca tgccacagaa cgccaactaa     360
ctcgagcac                                                            369

<210> SEQ ID NO 6
<211> LENGTH: 369
<212> TYPE: DNA
<213> ORGANISM: Homo sapiens

<400> SEQUENCE: 6
cacggatccg ctccgttccg cagcgcactg gagtcctctc cagccgaccc tgctaccctg      60
tctgaagacg aagcgcgtct gctgctggct gcgctggttc aggactacgt acagatgaag     120

```
gcggctgaac tggaacaaga acaggagcgc gaaggctcca gcctggattc cccgcgtagc    180
aaacgctgtg gcaacctgtc cacttgcatg ctgggtacct acacccaaga ctttaacaaa    240
tttcacacgt tccgcaaac tgctattggc gttggtgccc cgggtaagaa acgtgatatg     300
tctagcgacc tggaacgcga tcaccgcccg cacgttagca tgccgcagaa cgcaaattaa    360
ctcgagcac                                                            369

<210> SEQ ID NO 7
<211> LENGTH: 369
<212> TYPE: DNA
<213> ORGANISM: Homo sapiens

<400> SEQUENCE: 7
cacggatccg caccatttcg ttctgctctg aatcttctc ctgctgatcc tgcaaccctg      60
gctgaagacg aggcgcgtct gctgctggca gcactggttc aggattatgt tcagatgaaa    120
gcgagcgaac tggagcagga acaggagcgc gagggcagct ctctggattc tcctcgtagc    180
aaacgttgcg gtaacctgag cacctgcatg ctgggtacct acacgcaaga cttcaacaaa    240
ttccacactt tccgcagac tgcgattggt gtgggtgcgc cgggtaaaaa gcgtgacatg    300
agctctgacc tggaacgtga ccatcgtccg catgtttcta tgccgcagaa cgcgaactaa    360
ctcgagcac                                                            369

<210> SEQ ID NO 8
<211> LENGTH: 31
<212> TYPE: DNA
<213> ORGANISM: Artificial Sequence
<220> FEATURE:
<223> OTHER INFORMATION: Primer PCT-TB1-1

<400> SEQUENCE: 8
cacggatccg caccgttccg ttctgcgctg g                                    31

<210> SEQ ID NO 9
<211> LENGTH: 41
<212> TYPE: DNA
<213> ORGANISM: Artificial Sequence
<220> FEATURE:
<223> OTHER INFORMATION: Primer PCT-TB1-2

<400> SEQUENCE: 9
tggccggatc ggctggagag ctttccagcg cagaacggaa c                         41

<210> SEQ ID NO 10
<211> LENGTH: 41
<212> TYPE: DNA
<213> ORGANISM: Artificial Sequence
<220> FEATURE:
<223> OTHER INFORMATION: Primer PCT-TB1-3

<400> SEQUENCE: 10
cagccgatcc ggccaccctg agcgaagagg aagcgcgtct g                         41

<210> SEQ ID NO 11
<211> LENGTH: 41
<212> TYPE: DNA
<213> ORGANISM: Artificial Sequence
<220> FEATURE:
<223> OTHER INFORMATION: Primer PCT-TB1-4

<400> SEQUENCE: 11
tcctggacca gtgccgccag cagcagacgc gcttcctctt c                         41
```

<210> SEQ ID NO 12
<211> LENGTH: 41
<212> TYPE: DNA
<213> ORGANISM: Artificial Sequence
<220> FEATURE:
<223> OTHER INFORMATION: Primer PCT-TB1-5

<400> SEQUENCE: 12
cggcactggt ccaggactac gttcagatga aagcgtctga a                41

<210> SEQ ID NO 13
<211> LENGTH: 41
<212> TYPE: DNA
<213> ORGANISM: Artificial Sequence
<220> FEATURE:
<223> OTHER INFORMATION: Primer PCT-TB1-6

<400> SEQUENCE: 13
gttcctgttc ctgctccagt tcagacgctt tcatctgaac g                41

<210> SEQ ID NO 14
<211> LENGTH: 41
<212> TYPE: DNA
<213> ORGANISM: Artificial Sequence
<220> FEATURE:
<223> OTHER INFORMATION: Primer PCT-TB1-7

<400> SEQUENCE: 14
ctggagcagg aacaggaacg cgaaggtagc agcctggact c                41

<210> SEQ ID NO 15
<211> LENGTH: 41
<212> TYPE: DNA
<213> ORGANISM: Artificial Sequence
<220> FEATURE:
<223> OTHER INFORMATION: Primer PCT-TB1-8

<400> SEQUENCE: 15
taccacagcg cttggaacgt ggagagtcca ggctgctacc t                41

<210> SEQ ID NO 16
<211> LENGTH: 41
<212> TYPE: DNA
<213> ORGANISM: Artificial Sequence
<220> FEATURE:
<223> OTHER INFORMATION: Primer PCT-TB1-9

<400> SEQUENCE: 16
gttccaagcg ctgtggtaac ctgagcactt gtatgctggg c                41

<210> SEQ ID NO 17
<211> LENGTH: 41
<212> TYPE: DNA
<213> ORGANISM: Artificial Sequence
<220> FEATURE:
<223> OTHER INFORMATION: Primer PCT-TB1-10

<400> SEQUENCE: 17
ttgttgaagt cctgagtata ggtgcccagc atacaagtgc t                41

<210> SEQ ID NO 18
<211> LENGTH: 41
<212> TYPE: DNA
<213> ORGANISM: Artificial Sequence
<220> FEATURE:

<223> OTHER INFORMATION: Primer PCT-TB1-11

<400> SEQUENCE: 18
acctatactc aggacttcaa caagttccac actttcccgc a         41

<210> SEQ ID NO 19
<211> LENGTH: 41
<212> TYPE: DNA
<213> ORGANISM: Artificial Sequence
<220> FEATURE:
<223> OTHER INFORMATION: Primer PCT-TB1-12

<400> SEQUENCE: 19
gtgcgcccac accgatcgca gtctgcggga aagtgtggaa c         41

<210> SEQ ID NO 20
<211> LENGTH: 41
<212> TYPE: DNA
<213> ORGANISM: Artificial Sequence
<220> FEATURE:
<223> OTHER INFORMATION: Primer PCT-TB1-13

<400> SEQUENCE: 20
tcggtgtggg cgcaccgggt aagaaacgtg acatgagctc c         41

<210> SEQ ID NO 21
<211> LENGTH: 41
<212> TYPE: DNA
<213> ORGANISM: Artificial Sequence
<220> FEATURE:
<223> OTHER INFORMATION: Primer PCT-TB1-14

<400> SEQUENCE: 21
cggtggtcac gctccaggtc ggagctcatg tcacgtttct t         41

<210> SEQ ID NO 22
<211> LENGTH: 41
<212> TYPE: DNA
<213> ORGANISM: Artificial Sequence
<220> FEATURE:
<223> OTHER INFORMATION: Primer PCT-TB1-15

<400> SEQUENCE: 22
tggagcgtga ccaccgtcca catgtatcca tgccacagaa c         41

<210> SEQ ID NO 23
<211> LENGTH: 39
<212> TYPE: DNA
<213> ORGANISM: Artificial Sequence
<220> FEATURE:
<223> OTHER INFORMATION: Primer PCT-TB1-16

<400> SEQUENCE: 23
gtgctcgagt tagttggcgt tctgtggcat ggatacatg         39

<210> SEQ ID NO 24
<211> LENGTH: 30
<212> TYPE: DNA
<213> ORGANISM: Artificial Sequence
<220> FEATURE:
<223> OTHER INFORMATION: Primer PCT-TB2-1

<400> SEQUENCE: 24
cacggatccg ctccgttccg cagcgcactg         30

<210> SEQ ID NO 25
<211> LENGTH: 41
<212> TYPE: DNA
<213> ORGANISM: Artificial Sequence
<220> FEATURE:
<223> OTHER INFORMATION: Primer PCT-TB2-2

<400> SEQUENCE: 25
tagcagggtc ggctggagag gactccagtg cgctgcggaa c        41

<210> SEQ ID NO 26
<211> LENGTH: 41
<212> TYPE: DNA
<213> ORGANISM: Artificial Sequence
<220> FEATURE:
<223> OTHER INFORMATION: Primer PCT-TB2-3

<400> SEQUENCE: 26
ccagccgacc ctgctaccct gtctgaagac gaagcgcgtc t        41

<210> SEQ ID NO 27
<211> LENGTH: 41
<212> TYPE: DNA
<213> ORGANISM: Artificial Sequence
<220> FEATURE:
<223> OTHER INFORMATION: Primer PCT-TB2-4

<400> SEQUENCE: 27
cctgaaccag cgcagccagc agcagacgcg cttcgtcttc a        41

<210> SEQ ID NO 28
<211> LENGTH: 41
<212> TYPE: DNA
<213> ORGANISM: Artificial Sequence
<220> FEATURE:
<223> OTHER INFORMATION: Primer PCT-TB2-5

<400> SEQUENCE: 28
gctgcgctgg ttcaggacta cgtacagatg aaggcggctg a        41

<210> SEQ ID NO 29
<211> LENGTH: 41
<212> TYPE: DNA
<213> ORGANISM: Artificial Sequence
<220> FEATURE:
<223> OTHER INFORMATION: Primer PCT-TB2-6

<400> SEQUENCE: 29
cgcgctcctg ttcttgttcc agttcagccg ccttcatctg t        41

<210> SEQ ID NO 30
<211> LENGTH: 41
<212> TYPE: DNA
<213> ORGANISM: Artificial Sequence
<220> FEATURE:
<223> OTHER INFORMATION: Primer PCT-TB2-7

<400> SEQUENCE: 30
aacaagaaca ggagcgcgaa ggctccagcc tggattcccc g        41

<210> SEQ ID NO 31
<211> LENGTH: 41
<212> TYPE: DNA
<213> ORGANISM: Artificial Sequence
<220> FEATURE:
<223> OTHER INFORMATION: Primer PCT-TB2-8

<400> SEQUENCE: 31
caggttgcca cagcgtttgc tacgcgggga atccaggctg g          41

<210> SEQ ID NO 32
<211> LENGTH: 41
<212> TYPE: DNA
<213> ORGANISM: Artificial Sequence
<220> FEATURE:
<223> OTHER INFORMATION: Primer PCT-TB2-9

<400> SEQUENCE: 32
aacgctgtgg caacctgtcc acttgcatgc tgggtaccta c          41

<210> SEQ ID NO 33
<211> LENGTH: 44
<212> TYPE: DNA
<213> ORGANISM: Artificial Sequence
<220> FEATURE:
<223> OTHER INFORMATION: Primer PCT-TB2-10

<400> SEQUENCE: 33
gtgaaatttg ttaaagtctt gggtgtaggt acccagcatg caag        44

<210> SEQ ID NO 34
<211> LENGTH: 43
<212> TYPE: DNA
<213> ORGANISM: Artificial Sequence
<220> FEATURE:
<223> OTHER INFORMATION: Primer PCT-TB2-11

<400> SEQUENCE: 34
acccaagact ttaacaaatt tcacacgttt ccgcaaactg cta         43

<210> SEQ ID NO 35
<211> LENGTH: 41
<212> TYPE: DNA
<213> ORGANISM: Artificial Sequence
<220> FEATURE:
<223> OTHER INFORMATION: Primer PCT-TB2-12

<400> SEQUENCE: 35
ttacccgggg caccaacgcc aatagcagtt tgcggaaacg t          41

<210> SEQ ID NO 36
<211> LENGTH: 41
<212> TYPE: DNA
<213> ORGANISM: Artificial Sequence
<220> FEATURE:
<223> OTHER INFORMATION: Primer PCT-TB2-13

<400> SEQUENCE: 36
gttggtgccc cgggtaagaa acgtgatatg tctagcgacc t          41

<210> SEQ ID NO 37
<211> LENGTH: 41
<212> TYPE: DNA
<213> ORGANISM: Artificial Sequence
<220> FEATURE:
<223> OTHER INFORMATION: Primer PCT-TB2-14

<400> SEQUENCE: 37
gcgggcggtg atcgcgttcc aggtcgctag acatatcacg t          41

<210> SEQ ID NO 38
<211> LENGTH: 41

```
<212> TYPE: DNA
<213> ORGANISM: Artificial Sequence
<220> FEATURE:
<223> OTHER INFORMATION: Primer PCT-TB2-15

<400> SEQUENCE: 38
gcgatcaccg cccgcacgtt agcatgccgc agaacgcaaa t                    41

<210> SEQ ID NO 39
<211> LENGTH: 29
<212> TYPE: DNA
<213> ORGANISM: Artificial Sequence
<220> FEATURE:
<223> OTHER INFORMATION: Primer PCT-TB2-16

<400> SEQUENCE: 39
gtgctcgagt taatttgcgt tctgcggca                                  29

<210> SEQ ID NO 40
<211> LENGTH: 36
<212> TYPE: DNA
<213> ORGANISM: Artificial Sequence
<220> FEATURE:
<223> OTHER INFORMATION: Primer PCT-TB3-1

<400> SEQUENCE: 40
cacggatccg caccatttcg ttctgctctg aatct                           36

<210> SEQ ID NO 41
<211> LENGTH: 41
<212> TYPE: DNA
<213> ORGANISM: Artificial Sequence
<220> FEATURE:
<223> OTHER INFORMATION: Primer PCT-TB3-2

<400> SEQUENCE: 41
gttgcaggat cagcaggaga agattccaga gcagaacgaa a                    41

<210> SEQ ID NO 42
<211> LENGTH: 41
<212> TYPE: DNA
<213> ORGANISM: Artificial Sequence
<220> FEATURE:
<223> OTHER INFORMATION: Primer PCT-TB3-3

<400> SEQUENCE: 42
ctcctgctga tcctgcaacc ctggctgaag acgaggcgcg t                    41

<210> SEQ ID NO 43
<211> LENGTH: 41
<212> TYPE: DNA
<213> ORGANISM: Artificial Sequence
<220> FEATURE:
<223> OTHER INFORMATION: Primer PCT-TB3-4

<400> SEQUENCE: 43
cctgaaccag tgctgccagc agcagacgcg cctcgtcttc a                    41

<210> SEQ ID NO 44
<211> LENGTH: 41
<212> TYPE: DNA
<213> ORGANISM: Artificial Sequence
<220> FEATURE:
<223> OTHER INFORMATION: Primer PCT-TB3-5

<400> SEQUENCE: 44
```
ggcagcactg gttcaggatt atgttcagat gaaagcgagc g                41

<210> SEQ ID NO 45
<211> LENGTH: 41
<212> TYPE: DNA
<213> ORGANISM: Artificial Sequence
<220> FEATURE:
<223> OTHER INFORMATION: Primer PCT-TB3-6

<400> SEQUENCE: 45
gctcctgttc ctgctccagt tcgctcgctt tcatctgaac a                41

<210> SEQ ID NO 46
<211> LENGTH: 41
<212> TYPE: DNA
<213> ORGANISM: Artificial Sequence
<220> FEATURE:
<223> OTHER INFORMATION: Primer PCT-TB3-7

<400> SEQUENCE: 46
tggagcagga acaggagcgc gagggcagct ctctggattc t                41

<210> SEQ ID NO 47
<211> LENGTH: 41
<212> TYPE: DNA
<213> ORGANISM: Artificial Sequence
<220> FEATURE:
<223> OTHER INFORMATION: Primer PCT-TB3-8

<400> SEQUENCE: 47
taccgcaacg tttgctacga ggagaatcca gagagctgcc c                41

<210> SEQ ID NO 48
<211> LENGTH: 41
<212> TYPE: DNA
<213> ORGANISM: Artificial Sequence
<220> FEATURE:
<223> OTHER INFORMATION: Primer PCT-TB3-9

<400> SEQUENCE: 48
cgtagcaaac gttgcggtaa cctgagcacc tgcatgctgg g                41

<210> SEQ ID NO 49
<211> LENGTH: 41
<212> TYPE: DNA
<213> ORGANISM: Artificial Sequence
<220> FEATURE:
<223> OTHER INFORMATION: Primer PCT-TB3-10

<400> SEQUENCE: 49
tttgttgaag tcttgcgtgt aggtacccag catgcaggtg c                41

<210> SEQ ID NO 50
<211> LENGTH: 42
<212> TYPE: DNA
<213> ORGANISM: Artificial Sequence
<220> FEATURE:
<223> OTHER INFORMATION: Primer PCT-TB3-11

<400> SEQUENCE: 50
ctacacgcaa gacttcaaca aattccacac ttttccgcag ac                42

<210> SEQ ID NO 51
<211> LENGTH: 41
<212> TYPE: DNA
<213> ORGANISM: Artificial Sequence

```
<220> FEATURE:
<223> OTHER INFORMATION: Primer PCT-TB3-12

<400> SEQUENCE: 51
ggcgcaccca caccaatcgc agtctgcgga aaagtgtgga a                          41

<210> SEQ ID NO 52
<211> LENGTH: 41
<212> TYPE: DNA
<213> ORGANISM: Artificial Sequence
<220> FEATURE:
<223> OTHER INFORMATION: Primer PCT-TB3-13

<400> SEQUENCE: 52
tggtgtgggt gcgccgggta aaaagcgtga catgagctct g                          41

<210> SEQ ID NO 53
<211> LENGTH: 41
<212> TYPE: DNA
<213> ORGANISM: Artificial Sequence
<220> FEATURE:
<223> OTHER INFORMATION: Primer PCT-TB3-14

<400> SEQUENCE: 53
ggacgatggt cacgttccag gtcagagctc atgtcacgct t                          41

<210> SEQ ID NO 54
<211> LENGTH: 41
<212> TYPE: DNA
<213> ORGANISM: Artificial Sequence
<220> FEATURE:
<223> OTHER INFORMATION: Primer PCT-TB3-15

<400> SEQUENCE: 54
ggaacgtgac catcgtccgc atgtttctat gccgcagaac g                          41

<210> SEQ ID NO 55
<211> LENGTH: 37
<212> TYPE: DNA
<213> ORGANISM: Artificial Sequence
<220> FEATURE:
<223> OTHER INFORMATION: Primer PCT-TB3-16

<400> SEQUENCE: 55
gtgctcgagt tagttcgcgt tctgcggcat agaaaca                               37
```